(12) United States Patent
Li et al.

(10) Patent No.: US 12,349,959 B2
(45) Date of Patent: Jul. 8, 2025

(54) SURGICAL ELECTRODE ASSEMBLY

(71) Applicant: JIANGSU HOPE BIOMEDICAL SCIENCE & TECHNOLOGY CO., LTD., Yangzhou (CN)

(72) Inventors: Yuhua Li, Yangzhou (CN); Jianguo Cao, Yangzhou (CN)

(73) Assignee: Jiangsu Hope Biomedical Science &Technology Co., Ltd., Jiangsu (CN)

( * ) Notice: Subject to any disclaimer, the term of this patent is extended or adjusted under 35 U.S.C. 154(b) by 1076 days.

(21) Appl. No.: 17/273,273

(22) PCT Filed: Apr. 10, 2019

(86) PCT No.: PCT/CN2019/081999
§ 371 (c)(1),
(2) Date: Mar. 3, 2021

(87) PCT Pub. No.: WO2020/048127
PCT Pub. Date: Mar. 12, 2020

(65) Prior Publication Data
US 2021/0186597 A1   Jun. 24, 2021

(30) Foreign Application Priority Data

Sep. 4, 2018  (CN) .......................... 201811024436.9
Sep. 4, 2018  (CN) .......................... 201821446420.2

(51) Int. Cl.
*A61B 18/14* (2006.01)
*A61B 18/00* (2006.01)

(52) U.S. Cl.
CPC .............. *A61B 18/1442* (2013.01); *A61B 2018/00327* (2013.01); *A61B 2018/00589* (2013.01); *A61B 2018/1467* (2013.01); *A61B 2218/002* (2013.01)

(58) Field of Classification Search
CPC ...... A61B 18/1442; A61B 2018/00327; A61B 2018/00589; A61B 2018/1467;
(Continued)

(56) References Cited

U.S. PATENT DOCUMENTS

| 2011/0004157 A1 | 1/2011 | Dewaele et al. |
| 2013/0066317 A1* | 3/2013 | Evans ................. A61B 18/042 |
| | | 606/48 |

(Continued)

FOREIGN PATENT DOCUMENTS

| CN | 1810318 A | 8/2006 |
| CN | 103654694 A | 3/2014 |

(Continued)

OTHER PUBLICATIONS

Chinese International Search Report with Written Opinion mailed May 31, 2019, for PCT/CN2019/081999, 11 pages.

*Primary Examiner* — Linda C Dvorak
*Assistant Examiner* — Abigail Bock
(74) *Attorney, Agent, or Firm* — Morgan, Lewis & Bockius LLP (57) ABSTRACT

The present disclosure relates to a surgical electrode assembly comprising: an electrode device comprising electrodes; a manipulating device; an electrode driving device configured to drive the electrodes, the manipulating device comprising an actuation mechanism; an inner tube having an inner tube proximal portion at a proximal end thereof, an inner tube distal portion at a distal end thereof, and an inner tube bending portion therebetween, the inner tube bending portion having a curvature, such that the inner tube distal portion and the inner tube proximal portion are disposed at an angle to each other; an outer tube having an outer tube proximal portion at a proximal end thereof and an outer tube distal portion at a distal end thereof, and an outer tube connecting portion therebetween, wherein the outer tube (Continued)

connecting portion is adapted to the inner tube bending portion, such that when manipulating the manipulating device to cause the inner tube and the outer tube to move relative to each other, the outer tube connecting portion allows the inner tube bending portion of the inner tube and the outer tube to move relative to each other in the longitudinal direction without interfering of the inner tube bending portion of the inner tube with the outer tube proximal portion and the outer tube distal portion of the outer tube. The technical effect lies in that bending tubes are provided which can greatly improve the convenience of the surgical electrode assembly entering a human body channel, and the electrode assembly may not interfere with the instrument used in conjunction therewith.

15 Claims, 7 Drawing Sheets

(58) Field of Classification Search
CPC .......... A61B 2218/002; A61B 18/1445; A61B 18/1447; A61B 2018/00196
See application file for complete search history.

(56) References Cited

U.S. PATENT DOCUMENTS

| | | | |
|---|---|---|---|
| 2014/0005666 A1* | 1/2014 | Moua | A61B 18/1206 606/45 |
| 2017/0231481 A1 | 8/2017 | Kojo | |
| 2017/0325886 A1* | 11/2017 | Graham | A61B 18/1206 |

FOREIGN PATENT DOCUMENTS

| | | | | |
|---|---|---|---|---|
| CN | 104224317 A | * | 12/2014 | ............ A61B 18/14 |
| CN | 104434304 A | | 3/2015 | |
| CN | 105433896 A | | 3/2016 | |
| CN | 109009423 A | | 12/2018 | |
| CN | 109009424 A | | 12/2018 | |
| CN | 209269870 U | | 8/2019 | |
| JP | H 0843745 A | | 2/1996 | |
| WO | 0245589 A2 | | 6/2002 | |
| WO | WO-2017102975 A1 | * | 6/2017 | ......... A61B 18/1445 |
| WO | 2017/138533 A1 | | 8/2017 | |

\* cited by examiner

SURGICAL ELECTRODE ASSEMBLY

CROSS-REFERENCES TO RELATED APPLICATIONS

This application is a U.S. national phase application of a PCT Application No. PCT/CN2019/081999 filed on Apr. 10, 2019, which claims priority to a Chinese Patent Application No. 201811024436.9 filed in China on Sep. 4, 2018, and Chinese Patent Application No. 201821446420.2 filed in China on Sep. 4, 2018, the disclosure of which is incorporated herein by reference in its entirety.

TECHNICAL FIELD

The present disclosure relates to a hemostatic tool for surgery, in particular to a surgical electrode assembly.

BACKGROUND ART

At present, refinement and specialization of medical devices is a goal and trend. Electrocoagulation, as an efficient and reliable hemostasis method, is widely used in surgical operations. A surgical electrode assembly which is especially suitable for small-channel deep surgery such as minimally invasive microsurgery, neurosurgery, transnasal approach surgery, etc., is particularly adapted to be used with nasal endoscopy and ventriculoscopy, mainly for electrocoagulation to stop bleeding in minimally invasive microsurgery or neurosurgery. Since various operations have limited operating spaces, and further, the larger the surgical incision or channel, the greater the secondary injury to the patient, so that it is a constant pursuit to minimize the surgical channel and to be minimally invasive.

Bipolar coagulation forceps in various shapes are commonly used in existing surgical procedures. The core mechanics is to use fingers to close two jaws mounted in a fixture, around a blood vessel or tissue, to apply a high-frequency current through tips of the jaws to the part of the blood vessel or tissue caught therebetween, such that thermal effect of the high-frequency current causes the blood vessel wall to dehydrate and become wrinkled, and blood inside the blood vessel to coagulate, such that the blood vessel and blood clots merge, to thereby achieve effective hemostasis. Since jaws of ordinary bipolar coagulation forceps are wide and have a large volume in structure, and there is a maximal distance of at least 10 mm between front shanks of the two jaws entering a human body, but with a limited length, it is not suitable for hemostasis on a minimally invasive wound or a wound deep into a tissue that is accessed through a small channel (such as transnasal approach, ventricoscopy, etc.), and is especially limited when used in minimally invasive microsurgery and neurosurgery. Further, the larger volume of the jaws entering the human body prevents it from being used in conjunction with another instrument. Furthermore, since the jaws of ordinary bipolar coagulation forceps have a rather long protruding portion, the tips thereof are often prone to misalignment when being closed, which affects the effect and efficiency of coagulation.

An existing surgical electrode assembly allows the electrode tips to come close and away from one another through cooperation of an inner tube and an outer tube.

Since the inner tube and outer tube having different diameters may have slightly different bending curvatures when they are bent at the same time, which causes the outer tube, especially on a convex side thereof, to press tightly against a convex side of the inner tube, such that, when the outer tube moves relative to the inner tube, a significant increase in friction may occur, and even seizure may occur. This leads to a significant limitation in the degree of bendability of the inner and outer tubes such that it is impossible to ideally avoid the interference between a handle thereof and the other instrument used together by bending, and if they are slightly over bent, it may greatly increase the friction and reduce the operating sensitivity of the electrodes, which will affect the efficiency of the operation.

Besides, means for driving the outer tube of the existing surgical electrode assembly includes a handle spring leaf. When the handle is released, a screw plug and the outer tube retreat with action of elasticity of the spring leaf, such that the spring leaf needs to have a high elasticity and in order to ensure the elasticity, it is designed to have a relatively large width, but the spring leaf usually cannot provide a sufficient spring restoring force due to its structure, which may reduce the operating sensitivity of the electrode assembly and hinder the efficiency of the operation. Besides, due to the need to design a larger width of handle spring leaves in order to ensure the elasticity, the operator may often undesirably have his middle finger caught when pressing the two handle spring leaves with his thumb and index finger, which greatly hinders the comfort, safety and convenience of operation.

In addition, electrode sleeves of an existing surgical electrode assembly may be easily worn by the outer tube. Especially in the case of a ventricle mirror electrode assembly, walls of the electrode sleeves are more likely to be worn out due to their non-wear-resistant material and small thickness such that insulation ability thereof is damaged. In a common solution, it may be considered to try to use another material to form the electrode sleeves. However, due to the special structural requirements therefor, it is difficult to find a good wear-resistant material to form the electrode sleeves, and the development to use of material is usually very time-consuming and costly. Therefore, there is an urgent need for electrode sleeves that can protect the electrodes in a simple, reliable and low-cost manner, and reduce or even completely avoid the wear of the electrode sleeves by the outer tube.

And further, especially in the case of a ventricular mirror electrode assembly, the electrode tips are better to be small to improve accuracy of the operation, but small electrode tips are more likely to have their vision be obscured by the outer tube during the operation, which will also reduce accuracy, convenience, comfortability of the operation.

SUMMARY OF THE INVENTION

Therefore, the present disclosure aims to provide a surgical electrode assembly that can solve at least one of the above-mentioned problems existing in the prior art.

According to one aspect of the present disclosure, there is provided a surgical electrode assembly, the electrode assembly having a distal end farther away from an operator when in use and a proximal end closer to the operator when in use. The electrode assembly comprises an electrode device, a manipulating device, and an electrode driving device. The electrode device is disposed at a distal end of the electrode assembly, the electrode device comprising a first electrode and a second electrode, the first electrode and the second electrode being movable between a first position away from each other and a second position close to each other. The manipulating device is disposed at a proximal end of the electrode assembly and is configured to manipulate operation of the electrode device. The electrode driving device is disposed between the manipulating device and the electrode device, configured to drive the first electrode and the second electrode of the electrode device to move between the first position and the second position with action of the manipulating device. The manipulating device comprises a housing and an actuation mechanism at least partially disposed in the housing, and the actuation mechanism is adapted to actuate the electrode driving device. The actuation mechanism comprises a crank device, a slider device operatively connected with the crank device, and a damping device. The slider device has a rest position and a working position. When there is no external force applied, damping effect of the damping device renders the slider device in the rest position, the slider device being operatively connected to the electrode driving device, and in the rest position of the slider device, the first electrode and the second electrode are in the first position away from each other. An operator can apply a force to the crank device which in turn urges the slider device, such that the slider device is movable toward the working position, against the damping effect of the damping device, to thereby cause the first electrode and the second electrode of the electrode device to move from the first position to the second position.

The following technical effects, for example, can be produced with a surgical electrode assembly according to the present disclosure: the surgical electrode assembly ensures a sufficient actuation force including a restoring force, is more ergonomic, greatly improves operating sensitivity thereof, and therefore greatly improved surgical procedure efficiency, safety and manipulating comfortability.

According to one embodiment of the present disclosure, when the operator no longer applies a force to the crank device, the slider device moves toward the rest position with the action of the restoring force of the damping device, such that the first electrode and the second electrode of the electrode device move from the second position to the first position with action of their own elastic force, wherein the slider device urges and restores the crank device while moving toward the rest position.

According to one embodiment of the present disclosure, the electrode driving device comprises an inner tube and an outer tube configured to move relative to one another in a longitudinal direction.

According to one embodiment of the present disclosure, the inner tube has a distal end connected to proximal ends of the first electrode and the second electrode, the outer tube being disposed over the inner tube, and having a distal end abutting against the first electrode and the second electrode, such that the inner tube and the outer tube are adapted to move the first electrode and the second electrode between the first position and the second position.

According to one embodiment of the present disclosure, the slider device is operatively connected with the outer tube, such that the outer tube is movable with the movement of the slider device.

According to one embodiment of the present disclosure, the slider device is operatively connected with the inner tube, such that the inner tube is movable along with the movement of the slider device.

According to one embodiment of the present disclosure, the damping device is arranged between the slider device and the housing.

According to one embodiment of the present disclosure, the damping device is a coil spring or a hollow elastic body.

According to one embodiment of the present disclosure, the slider device has a distal portion with a smaller radial size, a proximal portion with a larger radial size, and a shoulder between the distal portion and the proximal portion, and the coil spring or hollow elastic body is configured to be disposed over the distal portion of the slider device and abuts against the shoulder.

According to one embodiment of the present disclosure, the manipulating device further comprises a fixing block for fixing the inner tube in the housing, the fixing block being disposed at a distance proximal to the slider device.

According to one embodiment of the present disclosure, the proximal end of the inner tube extends into and is fixed to a longitudinal through hole of the fixing block.

According to one embodiment of the present disclosure, the fixing block is provided with a lateral through hole that extends from an outer circumferential surface of the fixing block to the longitudinal through hole of the fixing block, wherein a fastening element is adapted to be introduced into the lateral through hole and pressed against the inner tube.

According to one embodiment of the present disclosure, the fastening element is a screw or rivet.

According to one embodiment of the present disclosure, the outer tube has a proximal opening formed with a flange, the hollow slider device is provided with a corresponding groove on an inner circumferential surface thereof, and the proximal end of the outer tube is fixed in a form-fit manner to the slider device through the flange and the groove.

According to one embodiment of the present disclosure, the slider device is provided with a guide, and the housing is provided with a mating guide for cooperating with said guide.

According to one embodiment of the present disclosure, said guide consists of guide pieces protruding from the slider device, and the mating guide consists of mating guide pieces protruding from an inner circumferential surface of the housing.

According to one embodiment of the present disclosure, a stop for limiting a maximum sliding distance of the slider device is provided at each end of the mating guide pieces.

According to one embodiment of the present disclosure, the housing comprises an upper housing and a lower housing that are molded or additively manufactured.

According to one embodiment of the present disclosure, a crank device is provided on each side of the housing.

According to one embodiment of the present disclosure, the crank device comprises a crank and a link, the link having a distal end pivotally connected to the common slider device, and a proximal end pivotally connected to a distal end of the corresponding crank, and a proximal end of the crank being pivotally connected to a common cylinder protruding from the inner circumference of the housing.

According to one embodiment of the present disclosure, the common cylinder has a slot formed in a center thereof, and a wire connected to the electrode is adapted to pass through the slot.

According to one embodiment of the present disclosure, the crank is designed to be an elongate and narrow press handle.

According to one embodiment of the present disclosure, inside the inner tube, or between the inner tube and the outer tube, or outside the outer tube, a delivery passage for delivering a flushing liquid is provided.

According to one embodiment of the present disclosure, the first electrode and the second electrode are fixed to the inner tube by an adhesive.

According to one embodiment of the present disclosure, the adhesive is epoxy glue.

According to one embodiment of the present disclosure, the inner tube is pressed flat at the first electrode and the second electrode extending into the inner tube, such that the inner tube, the first electrode and the second electrode are pressed together.

According to one embodiment of the present disclosure, the distal opening of the outer tube is formed with an outward flange.

According to one embodiment of the present disclosure, the distal portions of the first electrode and the second electrode are bent upward, downward or formed straight.

According to one embodiment of the present disclosure, a clamping surface of the distal portion of each of the first and second electrodes for clamping a target tissue of a human body forms a step on a transition portion to the proximal portion of the first or second electrode, the steps being configured to prevent the electrode sleeves on the proximal portions of the electrodes from contacting each other during a process of closing the first electrode and the second electrode.

According to one embodiment of the present disclosure, the distal portions of the first electrode and the second electrode are treated to prevent electrocoagulation and adhesion.

According to one embodiment of the present disclosure, the distal end of the outer tube has a flat tapered structure, the flat tapered structure including planes extending forward to gradually approach a centerline of the outer tube, and the planes being substantially perpendicular to the clamping surfaces for clamping the target tissue of the human body, of the distal portions of the first electrode and second electrode.

According to one embodiment of the present disclosure, the inner tube is pressed flat at the first electrode and the second electrode extending into the inner tube, such that the inner tube is pressed together with the first electrode and the second electrode, and then the first electrode and the second electrode are further fixed with the inner tube by injecting an adhesive into the inner tube.

According to another aspect of the present disclosure, there is provided a surgical electrode assembly, the electrode assembly having a distal end farther away from an operator when in use and a proximal end closer to the operator when in use. The electrode assembly comprises an electrode device, a manipulating device, and an electrode driving device. The electrode device is disposed at a distal end of the electrode assembly, the electrode device comprising a first electrode and a second electrode, the first electrode and the second electrode being movable between a first position away from each other and a second position close to each other. The manipulating device is disposed at a proximal end of the electrode assembly and is configured to manipulate operation of the electrode device. The electrode driving device is disposed between the manipulating device and the electrode device, configured to drive the first electrode and the second electrode of the electrode device to move between the first position and the second position with action of the manipulating device. The electrode driving device comprises an outer tube and an inner tube, wherein an outer diameter of the inner tube is smaller than an inner diameter of the outer tube, such that the inner tube is received inside the outer tube, such that the inner tube and the outer tube are movable relative to one another in a longitudinal direction of the inner tube and the outer tube. The inner tube has an inner tube proximal portion at a proximal end thereof, an inner tube distal portion at a distal end thereof, and an inner tube bending portion between the inner tube proximal portion and the inner tube distal portion. The inner tube bending portion has a curvature, such that the inner tube distal portion and the inner tube proximal portion are disposed at an angle to each other, and the outer tube has an outer tube proximal portion at a proximal end thereof and an outer tube distal portion at a distal end thereof, and an outer tube connecting portion between the outer tube proximal end portion and the outer tube distal end portion. The outer tube connecting portion is adapted to the inner tube bending portion, such that when manipulating the manipulating device to cause the inner tube and the outer tube to move relative to each other, the outer tube connecting portion allows the inner tube bending portion of the inner tube and the outer tube to move relative to each other in the longitudinal direction without interfering of the inner tube bending portion of the inner tube with the outer tube proximal portion and the outer tube distal portion of the outer tube.

The following technical effects, for example, can be produced by the surgical electrode assembly: bending tubes are provided which can greatly improve the convenience of the surgical electrode assembly entering a human body channel during a surgical procedure, and reduce undesired touching or even scratching of tissues of the human body channel by the surgical electrode assembly during the surgical procedure, and further, based on such bending, the handle portion of the electrode assembly may not interfere with the instrument such as an aspirator, used simultaneously. The surgical electrode assembly greatly reduces large friction or even seizure when the inner tube and the outer tube move relative to each other in the longitudinal direction with a relatively great bending, thereby greatly improving the operating sensitivity and operating accuracy of the surgical electrode assembly during a surgical procedure, and these advantages are of essential importance to successful completion of the surgical procedure.

According to one embodiment of the present disclosure, the outer tube connecting portion is a tubular portion having an opening on the outer tube and is formed in one piece with the outer tube proximal portion and the outer tube distal end portion, and the inner tube bending portion is configured to be at least partially exposed from the opening.

According to one embodiment of the present disclosure, when manipulating the manipulating device to cause the inner tube and the outer tube to move relative to each other, the opening is longitudinally and circumferentially sized to allow the inner tube bending portion of the inner tube to smoothly perform a relative movement in the longitudinal direction between the outer tube proximal portion and the outer tube distal portion of the outer tube without interfering with the outer tube proximal portion and the outer tube distal portion of the outer tube.

According to one embodiment of the present disclosure, when viewed into a cross section of the outer tube, the opening of the outer tube connecting portion occupies at least half of a circumference of the outer tube and exposes a convex side of the inner tube bending portion.

According to one embodiment of the present disclosure, a portion of the inner tube distal portion and/or a portion of the inner tube proximal portion are/is exposed from the opening of the outer tube connecting portion.

According to one embodiment of the present disclosure, there is always a distance from a distal edge and a proximal edge of the opening of the outer tube connecting portion to an apex of the inner tube bending portion when in use.

According to one embodiment of the present disclosure, the distal edge and/or the proximal edge of the opening are curled inward or encapsulated, such that the distal edge and/or the proximal edge of the opening do not scratch the human body target tissue when contacting the human body target tissue.

According to one embodiment of the present disclosure, the outer tube connecting portion and the outer tube distal portion are separately made parts and are fixedly connected in a mounted state, and/or the outer tube connecting portion and the outer tube proximal portion are separately made parts and are fixedly connected in a mounted state.

According to one embodiment of the present disclosure, the fixed connection is realized by riveting, threaded connection, welding and/or bonding.

According to one embodiment of the present disclosure, the outer tube connecting portion extends around all or part of the circumference of the inner tube.

According to one embodiment of the present disclosure, the outer tube connecting portion includes at least one curved rod and/or at least one curved flat plate and/or at least one curved plate that is curved in a transverse direction.

According to one embodiment of the present disclosure, the inner tube bending portion has a bending degree and the outer tube connecting portion has a bending degree that are variable simultaneously.

According to one embodiment of the present disclosure, the inner tube bending portion and the outer tube connecting portion are each made of a flexible material in order to allow the variation of the bending degree.

According to one embodiment of the present disclosure, the bending degree of the inner tube bending portion and the bending degree of the outer tube connecting portion are variable in a range between 10° and 60°.

According to one embodiment of the present disclosure, the bending degree of the inner tube bending portion and the bending degree of the outer tube connecting portion are variable in a range between 30° and 40°.

According to one embodiment of the present disclosure, the surgical electrode assembly enters a human body through a nose thereof.

According to one embodiment of the present disclosure, inside the inner tube, or between the inner tube and the outer tube, or outside the outer tube, a delivery passage for delivering a flushing liquid is provided.

According to one embodiment of the present disclosure, the first electrode and the second electrode are fixed to the inner tube by an adhesive.

According to one embodiment of the present disclosure, the adhesive is epoxy glue.

According to one embodiment of the present disclosure, the inner tube is pressed flat at the first electrode and the second electrode extending into the inner tube, such that the inner tube, the first electrode and the second electrode are pressed together.

According to one embodiment of the present disclosure, the distal opening of the outer tube is formed with an outward flange.

According to one embodiment of the present disclosure, the distal portions of the first electrode and the second electrode are bent upward, downward or formed straight.

According to one embodiment of the present disclosure, a clamping surface of the distal portion of each of the first and second electrodes for clamping a target tissue of a human body forms a step on a transition portion to the proximal portion of the first or second electrode, the steps being configured to prevent the electrode sleeves on the proximal portions of the electrodes from contacting each other during a process of closing the first electrode and the second electrode.

According to one embodiment of the present disclosure, the distal portions of the first electrode and the second electrode are treated to prevent electrocoagulation and adhesion.

According to one embodiment of the present disclosure, the distal end of the outer tube has a flat tapered structure, the flat tapered structure including planes extending forward to gradually approach a centerline of the outer tube, and the planes being substantially perpendicular to the clamping surfaces for clamping the target tissue of the human body, of the distal portions of the first electrode and second electrode.

According to one embodiment of the present disclosure, the inner tube is pressed flat at the first electrode and the second electrode extending into the inner tube, such that the inner tube is pressed together with the first electrode and the second electrode, and then the first electrode and the second electrode are further fixed with the inner tube by injecting an adhesive into the inner tube.

According to another aspect of the present disclosure, there is provided a surgical electrode assembly, the electrode assembly having a distal end farther away from an operator when in use and a proximal end closer to the operator when in use. The electrode assembly comprises an electrode device, an inner tube and an outer tube. The electrode device is disposed at a distal end of the electrode assembly, the electrode device comprising a first electrode and a second electrode, the first electrode and the second electrode being movable between a first position away from each other and a second position close to each other. The distal end of the inner tube is fixedly connected to the proximal end of the first electrode and the second electrode. The outer tube is disposed to have the inner tube received therein and has a distal end abutting against outer sides of bending proximal portions of the first electrode and the second electrode, such that relative movement of the inner tube and the outer tube in a longitudinal direction causes a movement of the first electrode and the second electrode between the first position and the second position. Distal to the inner tube, at least outside the electrode sleeves of the first electrode and the second electrode, a wear-resistant protection element is provided on at least a portion of the electrode sleeves of the first electrode and the second electrode, and when the inner tube and the outer tube move relatively in the longitudinal direction, a front end of the outer tube is slidable on the wear-resistant protective element.

The following technical effect, for example, can be produced by the surgical electrode assembly: a wear-resistant protective element is provided, which simply and effectively solves the technical problem that electrode sleeves of electrodes may be easily worn by the outer tube. Especially in the case of a ventricle mirror electrode assembly, walls of the electrode sleeves have a small thickness and are more likely to be worn out such that insulation ability thereof is damaged. In a common solution, one may usually try to use another material to form the electrode sleeve of the electrode. However, due to the special requirements for electrode sleeves of a ventricle mirror electrode assembly, it is difficult to realize and is very costly, and it is difficult to find an ideal electrode sleeve material. However, the wear-resistant protective element of this embodiment can protect the electrode sleeves of the electrode in a simple, reliable and low-cost manner, such that there is no need at all to consider the wear resistance of the electrode sleeve material, which broadens the material selection range.

According to one embodiment of the present disclosure, the wear-resistant protective element extends from the distal end of the inner tube and is made in one piece with the inner tube, and the wear-resistant protective element is fixedly connected with the electrode sleeves in the mounted state.

According to one embodiment of the present disclosure, the wear-resistant protective element and the inner tube are separately made parts, the wear-resistant protective element has a proximal end fixedly connected with a distal end of the inner tube in the mounted state, and the wear-resistant protective element is fixedly connected with the electrode sleeve in the mounted state.

According to one embodiment of the present disclosure, the wear-resistant protective element and the inner tube are separately made parts that are not connected to one another, and the wear-resistant protective element is fixedly connected with the electrode sleeves in the mounted state.

According to one embodiment of the present disclosure, the wear-resistant protective element is formed of a wear-resistant material.

According to one embodiment of the present disclosure, the wear-resistant protective element is formed of stainless steel.

According to one embodiment of the present disclosure, the fixed connection between the wear-resistant protective element and the electrode sleeves is realized by bonding, hot-melt connection or encapsulation injection molding.

According to one embodiment of the present disclosure, the fixed connection between the wear-resistant protective element and the inner tube is realized by riveting, threaded connection, welding and/or bonding.

According to one embodiment of the present disclosure, the distal end of the outer tube has a flat tapered structure, the flat tapered structure including planes extending forward to gradually approach a centerline of the outer tube, and the planes being substantially perpendicular to the clamping surfaces for clamping the target tissue of the human body, of the distal portions of the first electrode and second electrode.

According to one embodiment of the present disclosure, the surgical electrode assembly is used in conjunction with a ventricular mirror.

According to one embodiment of the present disclosure, inside the inner tube, or between the inner tube and the outer tube, or outside the outer tube, a delivery passage is provided for delivering a flushing liquid is provided.

According to one embodiment of the present disclosure, the first electrode and the second electrode are fixed to the inner tube by an adhesive.

According to one embodiment of the present disclosure, the adhesive is epoxy glue.

According to one embodiment of the present disclosure, the inner tube is pressed flat at the first electrode and the second electrode extending into the inner tube, such that the inner tube, the first electrode and the second electrode are pressed together.

According to one embodiment of the present disclosure, the distal opening of the outer tube is formed with an outward flange.

According to one embodiment of the present disclosure, the distal portions of the first electrode and the second electrode are bent upward, downward or formed straight.

According to one embodiment of the present disclosure, a clamping surface of the distal portion of each of the first and second electrodes for clamping a target tissue of a human body forms a step on a transition portion to the proximal portion of the first or second electrode, the steps being configured so as to prevent the electrode sleeves on the proximal portions of the electrodes from contacting each other during a process of closing the first electrode and the second electrode.

According to one embodiment of the present disclosure, each clamping surface has a length in a range between 2 mm and 4 mm.

According to one embodiment of the present disclosure, the distal portions of the first electrode and the second electrode are treated to prevent electrocoagulation adhesion.

According to one embodiment of the present disclosure, the fixed connection between the wear-resistant protective element and the electrode sleeves is realized by flaps on the wear-resistant protective element for encapsulating a circumference of the electrode sleeves.

According to one embodiment of the present disclosure, the inner tube is pressed flat at the first electrode and the second electrode extending into the inner tube, such that the inner tube is pressed together with the first electrode and the second electrode, and then the first electrode and the second electrode are further fixed with the inner tube by injecting an adhesive into the inner tube.

Other objects, features, and details of the present disclosure can be more fully understood with reference to the following detailed description of exemplary embodiments in conjunction with the accompanying drawings.

A person skilled in the art will understand advantages of corresponding embodiments and various additional embodiments by reading the following detailed description of the corresponding embodiments with reference to the drawings as included below. In addition, features in the drawings discussed below are not necessarily drawn to scale. Sizes of the features and elements in the drawings may be appropriately enlarged or reduced to more clearly illustrate the embodiments of the present disclosure.

DETAILED DESCRIPTION OF PREFERRED EMBODIMENTS

Various illustrative embodiments of the present disclosure are described below. In this description, for the sake of explanation only, various systems, structures and devices are schematically depicted in the drawings, but all the features of actual systems, structures and devices are not described. For example, well-known functions or structures are not described in detail to avoid unnecessary details to obscure the present disclosure. Of course, it should be understood that in any practical application, many specific implementation decisions need to be made to achieve the specific goals of the developer or user, and the system-related and industry-related restrictions need to be observed. These specific goals may vary with actual applications. In addition, it should be understood that although such specific implementation decisions are complicated and time-consuming, this is a routine task for those of ordinary skill in the art who benefit from the present application.

The terms and phrases used herein should be understood and interpreted as having a meaning consistent with the understanding of those terms and phrases by those skilled in the relevant art. The consistent usage of terms or phrases herein is not intended to imply a specific definition of the term or phrase, that is, a definition that differs from the ordinary and customary meanings understood by those skilled in the art. For terms or phrases intended to have a special meaning, that is, meanings different from those understood by the skilled person, this special definition will be clearly listed in the description by definition, giving special definition to the term or phrase directly and unambiguously.

In the present disclosure, unless otherwise clearly specified and defined, such terms as "mounted", "connected", "coupled", "connected", "fixed" and so on should be understood in a broad sense, for example, it can be a fixed connection or a it is a detachable connection, or an integral connection; it can be a mechanical connection or an electrical connection; it can be directly connected, or it can be indirectly connected through an intermediate medium, or it can be an internal communication between two components. Those of ordinary skill in the art can understand the specific meanings of the above terms in the present disclosure according to specific situations.

In the present disclosure, "distal" refers to a direction away from the operator when using the surgical electrode assembly of the present disclosure, and "proximal" refers to a direction close to the operator when using the surgical electrode assembly of the present disclosure.

Hereinafter, the embodiments of the present disclosure will be described in detail with reference to the accompanying drawings.

Figure 1:
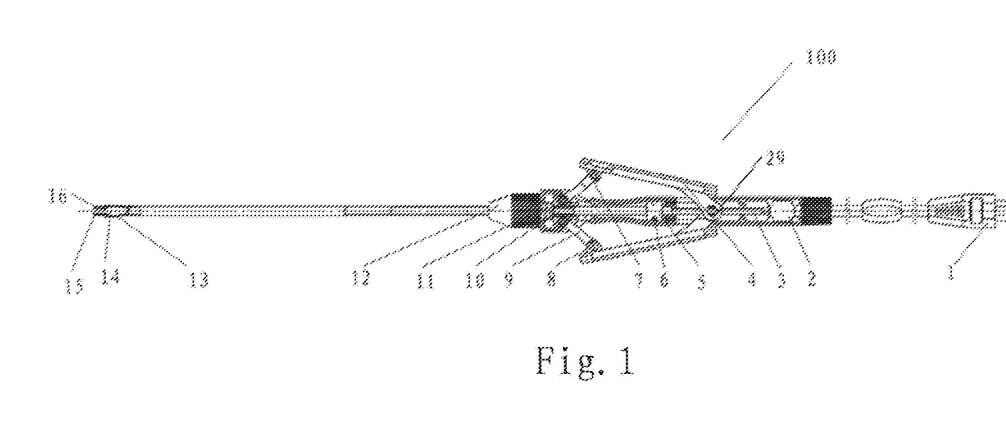
FIG. 1 shows a top view of a first embodiment of a surgical electrode assembly according to the present disclosure.
Figure 2:
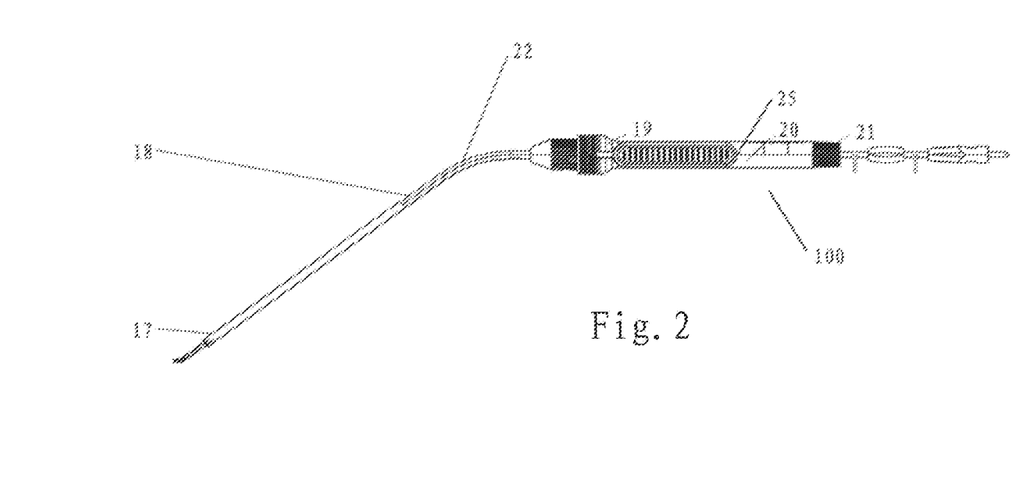
FIG. 2 shows a front view of the surgical electrode assembly as shown in FIG. 1.

FIG. 1 and FIG. 2 show a first embodiment of a surgical electrode assembly according to the present disclosure, the surgical electrode assembly being used in conjunction with a nasal mirror, which is referred hereto as a nasal mirror electrode assembly 100.

As shown in FIGS. 1 and 2, the nasal mirror electrode assembly 100 comprises: two electrodes 15, 16 and a wire 3 electrically connected to the electrodes 15, 16; an inner tube 18 fixed to proximal ends of the electrodes 15, 16; an outer tube 17 disposed to have the inner tube 18 received therein. The nasal mirror electrode assembly 100 further comprises a manipulating device 25 connected to the inner tube 18 and the outer tube 17, and the outer tube 17 is movable longitudinally relative to the inner tube 18 as actuated by the manipulating device 25. The wire 3 is connected to a high-frequency electric knife through a power line 1. The specific composition and connection manner of each component are described in detail as below.

The distal portions of the electrodes 15 and 16 are tips for operation, and the shape of the tips is designed to be curved upward (see FIG. 2), thereby reducing the obstruction of the field of view during the operation and thus facilitating the precise clamping of the human body target tissue. In another embodiment, the shape of the tip can also be designed to be curved downward or straight. The tips of the electrodes 15 and 16 are respectively provided with clamping surfaces on opposite inner sides thereof for clamping the target tissue of the human body. In order to reduce or avoid adhesion of the electrode tips and the target tissue of the human body during the operation, the electrode tips can be treated for anti-electrocoagulation adhesion.

The proximal portions of the electrodes 15 and 16 are curved and are provided with insulated electrode sleeves 13 and 14 respectively. A clamping surface of the distal tip of each electrode forms a step on a transition portion to the proximal portion of the electrode, to prevent the electrode sleeves 13, 14 on the proximal portions of the electrodes 13, 14 from contacting each other during a process of closing the electrodes 13, 14.

The proximal ends of the electrodes 15 and 16 are fixed to the inner tube 18. The inner tube 18 is provided with an opening (not shown, the opening may be a circular, oval or rectangular opening) for filling an adhesive (such as epoxy glue), and the adhesive is used to fix the proximal ends of the electrodes 15, 16 and adjacent portions of the wire 3 to the inner tube 18 to thereby prevent the electrodes 15 and 16 from moving in the inner tube 18. Further, the inner tube 18 can be pressed flat at the electrode extending into the inner tube 18 so as to press the inner tube 18 and the electrode 15, 16 together to further ensure the fixation of the electrode 15, 16 and the inner tube 18. The inner tube 18 and the electrode 15, 16 can be fixed in a manner as the following, i.e., firstly, pressing the inner tube 18 flat at the electrode 15, 16 extending into the inner tube 18 so as to press the inner tube 18 and the electrode 15, 16 together, and then, further fixing the electrode 15, 16 and the inner tube 18 by injecting an adhesive in the inner tube 18.

The outer tube 17 is disposed to have the inner tube 18 received therein, and the outer tube 17 is configured to move longitudinally relative to the inner tube 18, such that the electrodes 15 and 16 are movable radially away from each other to enter the first position or radially close to each other to enter the second position. Particularly, the electrodes 15, 16 are fixedly connected to the distal end of the inner tube 18. When the outer tube 17 moves distally relative to the inner tube 18, the electrodes 15, 16 are constrained in the outer tube 17, such that the electrodes 15, 16 move radially close to each other; when the outer tube 17 moves proximally relative to the inner tube 18, the electrodes 15, 16 are exposed from the outer tube 17, such that the electrodes 15, 16 are radially separated from each other based on their own elasticity.

In order to reduce the friction between the distal end of the outer tube 17 and the outer side of the electrode sleeves 13, 14 of the electrodes 15, 16, the distal opening of the outer tube 17 is formed with an outward flange, which is smooth at least at a portion thereof connected to the electrode sleeves 13, 14, thereby reducing abrasion of the distal end of the outer tube 17 to the outer side of the electrode sleeves 13 and 14.

The outer tube 17 has an outer diameter in a range of 1.5 to 3.5 mm, which is only $1/4$ to $1/3$ of the distance between two jaws of ordinary bipolar coagulation forceps, and has a length that can be more than 350 mm. Further, the electrodes 15, 16 are also thinner, and have an average thickness that is only $1/2$ to $2/3$ of the distal portion at the jaw tip of ordinary electrocoagulation forceps. Therefore, the nasal mirror electrode assembly according to the present disclosure is more suitable for transnasal small-channel deep surgery treatment.

In order to facilitate the introduction of the nasal mirror electrode assembly into the human body through the nose, based on the flexibility of the internal channel of the nasal cavity, the inner tube 18 has an inner tube proximal portion at a proximal end thereof, an inner tube distal portion of at a distal end thereof, and an inner tube bending portion therebetween. The inner tube bending portion has a curvature, such that the inner tube distal portion and the inner tube proximal portion are disposed at an angle to each other, and the outer tube 17 has an outer tube proximal portion 27 at a proximal end thereof and an outer tube distal portion 26 at a distal end thereof, and an outer tube connecting portion 28 therebetween (see FIG. 3).

When the inner tube 18 and the outer tube 17 having different diameters are bent at the same time, the bending curvatures of the inner tube 18 and the outer tube 17 are slightly different, such that a convex side of the outer tube 17 presses against a convex side of the inner tube 18, whereby a significantly increased friction force may be generated when they move relatively in the longitudinal direction, and even more, the relative longitudinal movement of the inner tube 18 and the outer tube 17 cannot be performed due to seizure. Therefore, in order to reduce friction when the inner tube 18 and the outer tube 17 move relative to each other in the longitudinal direction, especially the friction generated at a contact area of the convex sides of the inner tube 18 and outer tube 17, an opening 22 can be formed at least at a convex side of the outer tube connecting portion 28 of the outer tube 17 (see FIG. 3).

Figure 3:
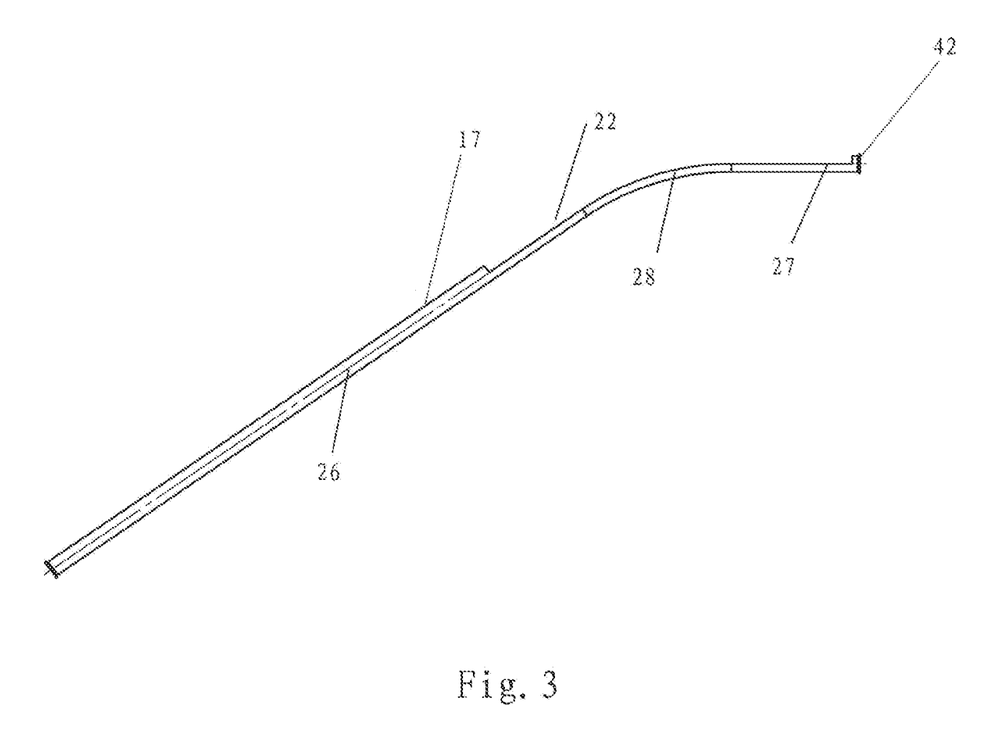
FIG. 3 shows a front view of an outer tube having an opening of the surgical electrode assembly as shown in FIG. 1.

The opening 22 is sized such that the widest portion of the inner tube 18 can leave the opening 22 without scratching an edge of the opening 22, thereby minimizing friction of the inner tube 18 with the outer tube 17 when the inner tube 18 and the outer tube 17 move relative to each other. When manipulating the manipulating device 25 to cause the inner tube 18 and the outer tube 17 to move relative to each other, the opening is longitudinally and circumferentially sized to allow the inner tube bending portion of the inner tube 18 to smoothly perform a relative movement in the longitudinal direction between the outer tube proximal portion 27 and the outer tube distal portion 26 of the outer tube 17 without interfering with the outer tube proximal portion 27 and the outer tube distal portion 26 of the outer tube 17.

When viewed into a cross section of the outer tube, the opening of the outer tube connecting portion 28 occupies substantially a half of a circumference of the outer tube and exposes a convex side, rather than a concave side of the inner tube bending portion, such that a contact area where friction is most likely to be produced between the inner tube 18 and the outer tube 17 is greatly reduced. In other words, when viewed into the cross section of the outer tube, an arc length of the outer tube portion left at the opening is roughly half of the circumference of the outer tube. The ratio "a half" is only one embodiment of the present disclosure. Of course, the opening can be designed to occupy more than a half or less than a half of the circumference of the outer tube as actually required, as long as the opening allows the inner tube bending portion of the inner tube 18 to smoothly perform a relative movement in the longitudinal direction between the outer tube proximal portion 27 and the outer tube distal portion 26 of the outer tube 17 without interfering with the outer tube proximal portion 27 and the outer tube distal portion 26 of the outer tube 17. Of course, whether to expose particularly the convex side or the concave side of the inner tube bending portion, it can be selected accordingly for the purpose of reducing friction as much as possible according to the actual application. In the embodiment as shown, the opening 22 may extend to only a small distance from the manipulating device 25. In some embodiments, the distance is less than 1 cm, preferably less than 0.5 cm.

In some embodiments, the circumferential length of the outer tube connecting portion 28 of the outer tube 17 at the portion where the opening 22 is formed is less than or equal to a half of the circumference of the outer tube 17 and thereby further ensures that there be no big friction when the inner tube 18 and the outer tube 17 move relatively to one another. The outer tube connecting portion 28 of the outer tube 17 and the inner tube bending portion of the inner tube 18 are at least partially spaced apart when the inner tube 18 and the outer tube 17 move relative to each other in the longitudinal direction, thereby reducing friction during relative movement in the longitudinal direction.

There should be always a distance from a distal edge and a proximal edge of the opening 22 to an apex of the inner tube bending portion of the inner tube 18 when in use. The distance is designed so that the distal edge and the proximal edge of the opening 22 are difficult to or will not come into contact with the target tissue of the human body when the electrode assembly is used, thereby reducing or eliminating the possibility of scratching the target tissue of the human body by the distal edge and the proximal edge of the opening 22 during surgery.

In some embodiments, the distal and proximal edges of the opening 22 are curled inward or encapsulated with a suitable material to greatly reduce the sharpness of the opening 22 to ensure that the distal and proximal edges of the opening 22 will not scratch the human body target tissue when coming into contact with the human body target tissue.

In some embodiments, the outer tube connecting portion 28 and the outer tube distal portion 27 and/or the outer tube proximal portion 26 are separately made parts, and the outer tube connecting portion 28 and the outer tube distal portion 27 and/or the outer tube proximal portion 26 are fixedly connected in the mounted state. The outer tube connecting portion 28 may be, for example, a rod or a plate with a bending portion. The outer tube connecting portion 28 is adapted to transmit a force from the manipulating device 25 to the outer tube distal portion 26 of the outer tube 17 with as little friction as possible, so as to allow the desired relative movement of the inner tube 18 and the outer tube 17 in the longitudinal direction. The outer tube connecting portion 27 is fixedly connected to the outer tube distal portion 26 and the outer tube proximal connecting portion 27 of the outer tube 17, for example, by riveting, screwing, welding and/or bonding. In some embodiments, the outer tube connecting portion 28 extends around all or part of the circumference of the inner tube bending portion of the inner tube 18.

Advantageously, the inner tube bending portion of the inner tube 18 and the outer tube connecting portion of the outer tube 17 are each formed of a flexible material, such that the inner tube bending portion has a bending degree and the outer tube connecting portion 28 has a bending degree that are variable simultaneously. The bending degree of the inner tube bending portion and the bending degree of the outer tube connecting portion 28 are variable in a range between 10° and 60°. After many experiments, it has been proved that, more advantageously, the bending degree of the inner tube bending portion and the bending degree of the outer tube connecting portion 28 are variable in a range between 30° and 40°. Therefore, the degree of curvature of the nasal mirror electrode assembly can be adjusted according to the actual needs of different operations and other instruments used in conjunction.

A delivery passage for delivering a flushing fluid, such as physiological saline, may be provided inside the inner tube 18, between the inner tube 18 and the outer tube 17, or outside the outer tube 17. In some embodiments, the delivery passage is provided inside the inner tube 18 or outside the outer tube 17 so as not to hinder the relative longitudinal movement of the inner tube 18 and the outer tube 17.

The manipulating device 25 can be held by an operator to enable the relative movement of the inner tube 18 and the outer tube 17 in the longitudinal direction. The manipulating device 25 comprises a housing and an actuation mechanism at least partially disposed in the housing.

As can be seen from FIGS. 1, 2, 4 and 6, the housing of the manipulating device 25 comprises an upper housing 19 and a lower housing 20. The two-piece housing enables simple and low-cost manufacturing. The upper housing 19 and the lower housing 20 can be molded or manufactured by an additive manufacturing method (3D printing method).

Figure 4:
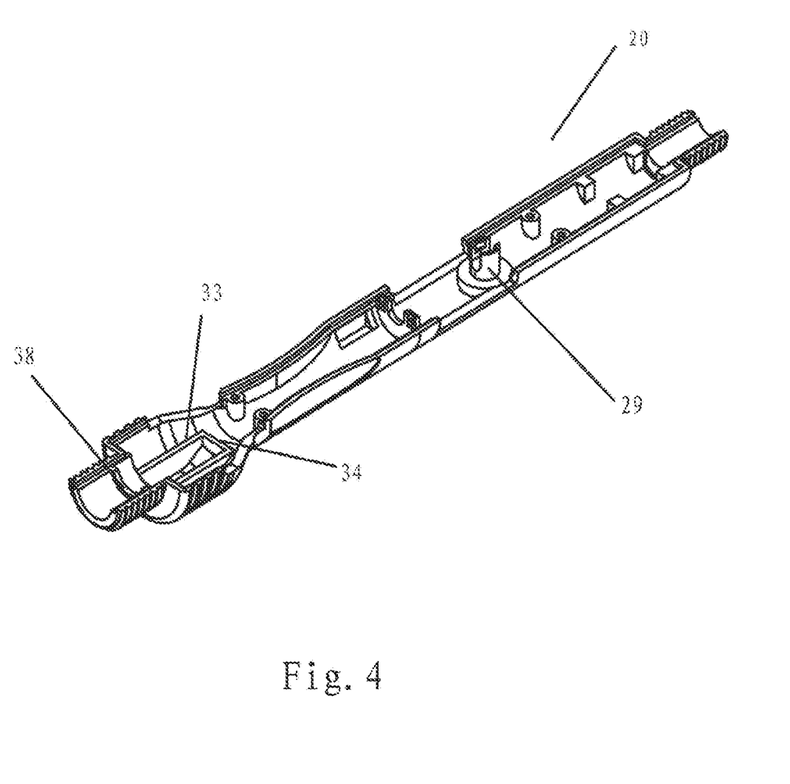
FIG. 4 shows a perspective view of a lower housing of a manipulating device of the surgical electrode assembly as shown in FIG. 1.
Figure 6:
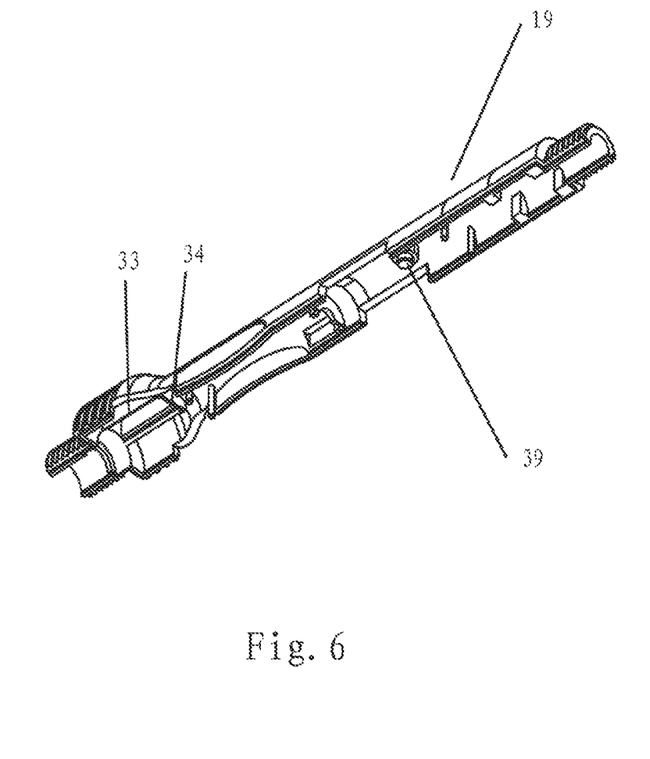
FIG. 6 shows a perspective view of an upper housing of the manipulating device of the surgical electrode assembly as shown in FIG. 1.

The upper housing 19 and the lower housing 20 are fixed with a front screw cap 12 at a front end thereof and a rear screw cap 21 at a rear end thereof. Therefore, the upper housing 19 and the lower housing 20 are formed with threads at the front and rear ends, and the threaded connection enables the upper housing 19 and the lower housing 20 to be fastened more reliably. Of course, another connection method can be provided here to connect the upper housing 19 and the lower housing 20 in a fixed manner, such as a clamp connection, a connection by screws or rivets, or the like. The upper housing 19 and the lower housing 20 can be connected at a middle thereof by internal buckles or catches on the outer circumference, threaded connection or riveting, and the connection in the middle can reliably prevent the elongate upper and lower housings 19, 20 from unwanted separation in the middle.

It can be seen from FIG. 1 that the housing includes a fixed block 5 for fixing the inner tube 18 in the housing. The fixing block 5 is locked in the housing, and therefore the fixing block 5 and the inner tube 18 cannot move relative to the housing.

It can be seen from FIG. 1 that the actuation mechanism includes a crank device, a slider device 10 that cooperates with the crank device, and a coil spring 11. The crank device comprises a crank 4 and a link 9. Instead of a spring element 11, another suitable damping device, such as a hollow elastic body, can be used. When the crank 4 is pressed, the slider device 10 is movable distally against the elastic force of the coil spring 11, and when the crank 4 is released, the slider device 10 is movable proximally with action of the elastic force of the coil spring 11.

It can be seen from FIG. 1 that the crank 4 and the link 9 are respectively provided at the connecting portion of the upper housing 19 and the lower housing 20 on both sides of the housing. The two cranks 4 are pivotally connected at their proximal ends to a cylinder 29 protruding from the lower housing 20. The proximal ends of the two links 9 are respectively pivotally connected to the distal ends of the cranks 4, and the distal ends of the two links 9 are pivotally connected to the protrusions 30 on both sides of a common slider device 10 (see FIG. 5). The slider device 10 is directly and fixedly connected with the outer tube 17 so as to enable a longitudinal movement of the outer tube 17 when the slider device 10 moves.

The fixing block 5 is located between the slider device 10 and the cylinder 29, and the slider device 10 is disposed at a distance from the fixing block 5 and is hollow. The inner tube 18 extends through the slider device 10 from distal to proximal and the proximal end of the inner tube 18 is fixed in the fixing block 5.

In some embodiments, the proximal end of the inner tube 18 extends into and passes through the longitudinal through hole (not shown) of the fixing block 5 and is fastened in the longitudinal through hole by a fastening element 6. Starting from the outer circumferential surface of the fixing block 5, a lateral through hole (not shown) is formed preferably perpendicular to the inner tube 18, the lateral through hole extending to a longitudinal through hole of the fixing block 5. The fastening element 6 is adapted to be introduced into the lateral through hole and pressed against the inner tube 18. The fastening element is for example, a screw or rivet.

The proximal end of the outer tube 17 is fixed to the slider device 10. In order to fix the outer tube 17 with the slider device 10, the proximal opening of the outer tube 17 is formed with a flange 42, and the slider device 10 is provided with a groove 31 (see FIG. 5) on an inner circumferential surface thereof, corresponding to the flange 42 formed on the proximal opening of the outer tube 17, such that the proximal end of the outer tube 17 is fixed in a form-fit manner to the slider device.

Figure 5:
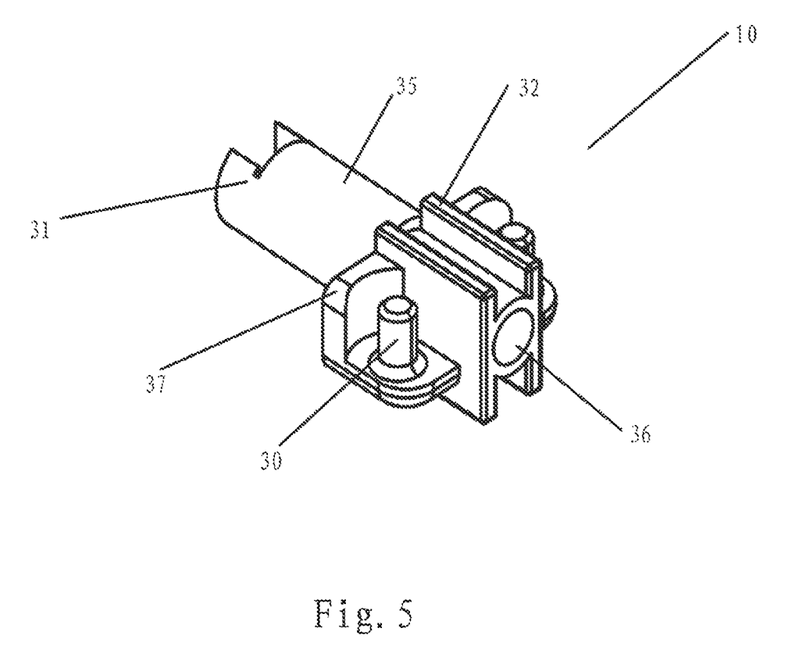
FIG. 5 shows a perspective view of a slider device of the manipulating device of the surgical electrode assembly as shown in FIG. 1.

The slider device 10 is provided with a guide 32 (see FIG. 5), and a mating guide 33 (see FIG. 4) for cooperating with the guide 32 is provided on an inner circumference of the housing, by means of cooperation of the guide 32 with the mating guide 33, the movement of the slider device 10 can be limited to a linear movement. Referring to FIG. 5, the guide 32 comprises four upper and lower facing guide pieces 32 protruding from the proximal portion 36 of the slider device 10 and extending along the longitudinal direction of the slider device 10. See FIG. 4 and FIG. 6, the mating guide 33 comprises two mating guide pieces 33 protruding from the inner circumferential surface of the lower housing 20 and two mating guide pieces protruding from the inner circumferential surface of the upper housing 19 that extend parallel to each other in the longitudinal direction of the housing. In the mounted state, the guide pieces 32 of the slider device abut respectively against the inner sides of the mating guide pieces 33 in the housing. At both ends of each two mating guide pieces 33, between the mating guide pieces 33, there is provided a stopper 34 that can be abutted by an end of the guide piece 32, and by means of the stopper 34, a maximum sliding distance of the slider device 10 is limited.

The distal portion 35 of the slider device 10 is configured to be in a cylindrical shape and forms a shoulder 37 with the proximal portion 36, whereby the coil spring 11 can be disposed around the cylindrical distal portion 35 of the slider device 10 and abut against the shoulder 37 at the proximal end, and a distal end of the coil spring 11 abuts against an annular flange 38 protruding from the inner circumference of the housing.

When the cranks 4 on both sides are pressed together, the two links 9 urge the slider device 10 and the outer tube 17 to move distally, and the outer tube 17 urges the two electrodes 15, 16 to complete a closing action. When the hand is released, the resilient force of the spring 11 is directly applied to the slider device 10 and returns it to position. At the same time, the slider device 10 urges the two cranks 4 back to the initial state while the two electrodes 15, 16 are spaced apart based on their own elasticity. As a result, the electrodes 15 and 16 come close to and get away from each other.

As can be seen from FIG. 4, the cylinder 29 protruding from the inner circumference of the housing is positioned at a central axis of the lower housing 20 and has a slot formed in a center thereof, the slot extending from a top of the cylinder 29 to a bottom thereof, and a wire 3 connected to the electrode 15, 16 is adapted to pass through the slot. As can be seen from FIG. 6, on a central axis of the upper housing 19, there is a corresponding cylinder 39 protruding from the inner circumference of the upper housing 19. In the mounted state, a free end of the corresponding cylinder 39 abuts against a free end of the cylinder 29 such that it can prevent the wire 3 from moving out of the slot of the cylinder 29 and can also have an effect of positioning the upper housing 19 and the lower housing 20 during mounting.

As can be seen from FIGS. 1 and 2, the crank 4 is designed as an elongate press handle and is designed to be so narrow that the middle finger will not be caught when the two cranks 4 are pressed with the thumb and index finger, thereby greatly improving the safety and convenience of operation. An anti-slip structure, such as a convex-concave structure, may be provided on the pressing surface of the crank 4.

As can be seen from FIG. 1, in the housing, between the cylinder 29 and the rear screw cap 21, an engagement block 2 is provided near the rear screw cap 21, the engagement block 2 being integrally formed with a power line, the engagement block 2 being engaged in a corresponding slot in the housing such that the power line 1 is reliably fixed in the housing. On a left side of the engagement block 2, conductor of the wire 3 and conductor of the power line 1 are welded together to enable an electrical connection therebetween.

The following technical effects, for example, can be produced with a nasal mirror electrode assembly according to the present disclosure: the surgical electrode assembly ensures the provision of a sufficient actuation force including a restoring force, is more ergonomic, greatly improves operating sensitivity thereof, and therefore greatly improves surgical procedure efficiency, safety and manipulating comfortability. Bending tubes are provided which can greatly improve the convenience of the nasal mirror electrode assembly entering a human body channel during a surgical procedure, and reduce undesired touching or even scratching of tissues of the human body channel by the nasal mirror electrode assembly during the surgical procedure, and further, based on such bending, the handle portion of the electrode assembly may not interfere with the instrument such as an aspirator, used in conjunction therewith. The bending degree is adjustable such that the nasal mirror electrode assembly can be better adapted to different surgical requirements and to any other instrument used in conjunction therewith such that they do not interfere with one another. And further, by providing an opening on the connecting portion of the outer tube or replacing the connecting portion of the outer tube with a connecting element, it greatly reduces large friction or even seizure when the inner tube and the outer tube move relative to each other in the longitudinal direction with a relatively great bending degree, thereby greatly improving the operating sensitivity and operating accuracy of the nasal mirror electrode assembly during a surgical procedure, and these advantages are of essential importance to successful completion of the surgical procedure.

FIG. 7 to FIG. 10 show a second embodiment of a surgical electrode assembly according to the present disclosure. The surgical electrode assembly is used in conjunction with a ventricular mirror and is referred hereto as a ventricular mirror electrode assembly 200. The manipulating device 1025 in this embodiment is substantially the same as the embodiment of the nasal mirror electrode assembly 100. One may refer to the related description of the manipulating device 25 of the nasal mirror electrode assembly 100 in the previous embodiment, and therefore, it will not be repeated here. Differences between this embodiment and the previous embodiment are mainly described as below.

Figure 7:
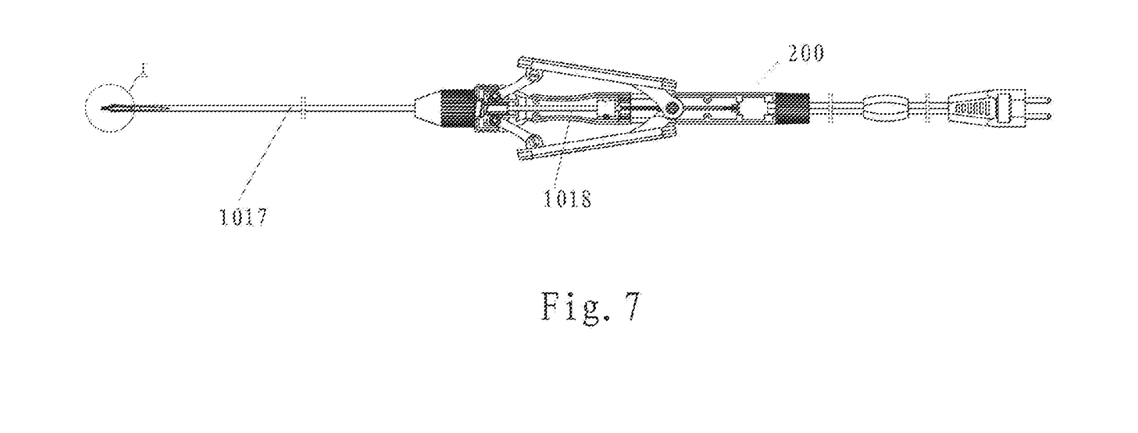
FIG. 7 shows a top view of a second embodiment of a surgical electrode assembly according to the present disclosure.
Figure 8:
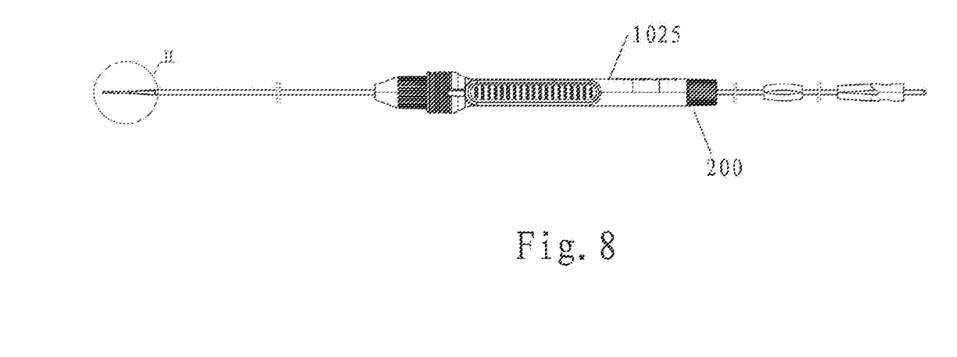
FIG. 8 shows a front view of the surgical electrode assembly as shown in FIG. 7.

FIGS. 7 and 8 respectively show a top view and a front view of the ventricle mirror electrode assembly 200. As can be seen, compared to the previous embodiment, in this embodiment, the inner tube 1018 and the outer tube 1017 are straight and thinner, the electrodes 1015, 1016 are also thinner and shorter, and the electrode tips are straight. Of course, the electrode tip can also be bent upward or downward as needed. The electrode sleeves 1013 and 1014 are correspondingly thinner.

Figure 9:
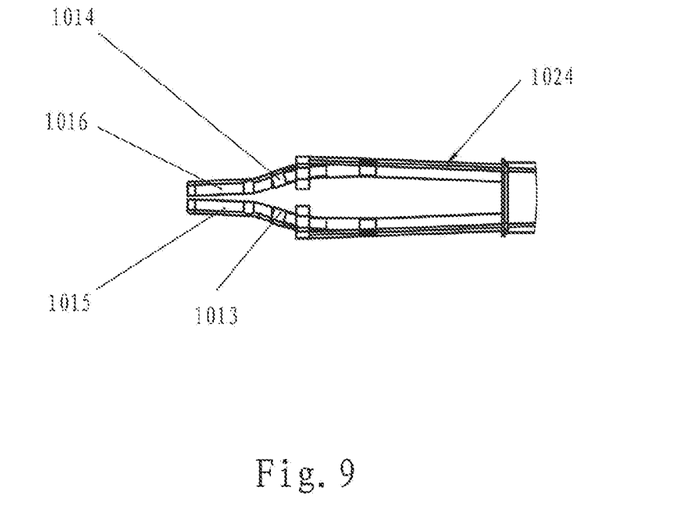
FIG. 9 shows an enlarged view of part I of the surgical electrode assembly as shown in FIG. 7.

FIG. 9 shows an enlarged view of part I as shown in FIG. 7. As can be seen from FIG. 9, distal to the inner tube 1018, on an outer side of the electrode sleeves 1013, 1014 of the electrodes, there is provided a wear-resistant protective element 1024 for protecting the electrode sleeves 1013, 1014. When the inner tube 1018 and the outer tube 1017 move relative to each other in the longitudinal direction, the distal end of the outer tube 1017 slides on the wear-resistant protective element, instead of sliding on the electrode sleeves 1013, 1014. Therefore, the wear-resistant protective element 1024 can protect the electrode sleeves 1013, 1014, and prevent the outer tube 1017 from scratching the outer side of the electrode sleeves 1013, 1014 and damaging the insulation ability of the electrode sleeves 1013, 1014 when the inner tube 1018 and the outer tube 1017 move relative to each other in the longitudinal direction. The wear-resistant protective element 1024 may be made of a wear-resistant material, for example stainless steel. The flange of the distal opening of the outer tube 1017 can be used together with the wear-resistant protective element 1024 to further protect the electrode sleeves 1013, 1014 from abrasion.

The wear-resistant protective element 1024 can extend from the distal end of the inner tube 1018 and be made in one piece with the inner tube 1018, and the wear-resistant protective element 1024 is fixedly connected with the electrode sleeves 1013, 1014 in the mounted state. In an alternative embodiment, the wear-resistant protective element 1024 and the inner tube 1018 are separately made parts, the wear-resistant protective element 1024 has a proximal end fixedly connected with a distal end of the inner tube 1018 in the mounted state, and the wear-resistant protective element 1024 is fixedly connected with the electrode sleeve 1013, 1014 in the mounted state. In an alternative embodiment, the wear-resistant protective element 1024 and the inner tube 1018 are separately made parts that are not connected to one another, and the wear-resistant protective element 1024 is fixedly connected with the electrode sleeves 1013, 1014 in the mounted state.

The fixed connection between the wear-resistant protective element 1024 and the inner tube 1018 may be realized by form-fitting, force-fitting and/or material-fitting, for example, it may be realized by riveting, screwing, welding and/or bonding. In this embodiment, the fixed connection between the wear-resistant protective member 1024 and the electrode sleeves 1013, 1014 is realized as follows, that is, a flap is provided on each side of the distal end of each wear-resistant protective member 1024, and during mounting, the flap encapsulates the circumference of the electrode sleeve 1013, 1014 or is wrapped wound on the electrode sleeve 1013, 1014, so as to realize the mechanically fixed connection between the wear-resistant protective member 1024 and the electrode sleeves 1013, 1014. Alternatively, the fixed connection can also be realized by bonding, hot-melt connection or encapsulation injection molding.

Figure 10:
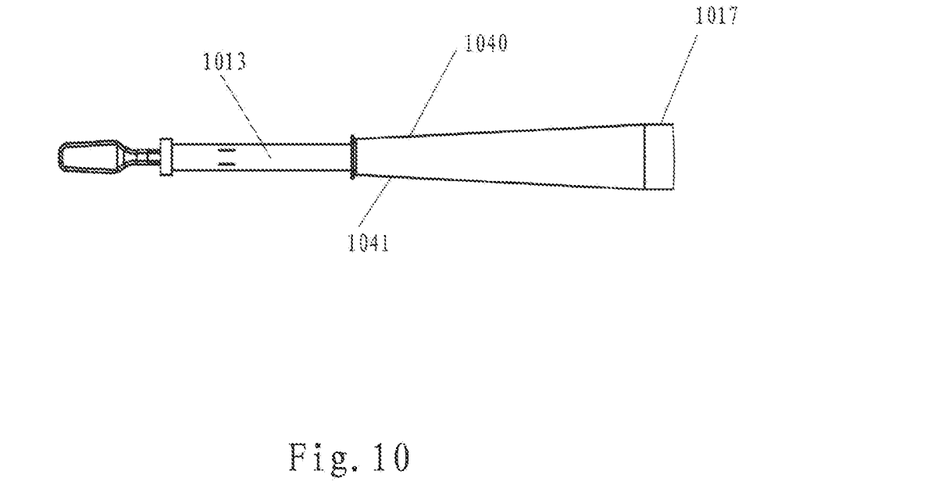
FIG. 10 shows an enlarged view of part II of the surgical electrode assembly as shown in FIG. 8.

FIG. 10 shows an enlarged view of part II as shown in FIG. 8. As can be seen from FIG. 10, the distal end of the outer tube 1017 has a flat tapered structure 1040, the flat tapered structure 1040 including two planes extending forward to gradually approach a centerline of the outer tube, and the planes 1041 being substantially perpendicular to the clamping surfaces for clamping the target tissue of the human body, on inner sides of the electrode tips. After many experiments, it has been proved that, the flat tapered structure 1040 at the distal end of the outer tube can effectively prevent the outer tube 1017 from blocking the field of view and causing inconvenience in operation, thereby greatly improving the convenience and accuracy of the operation. This is particularly advantageous when the electrode tips are straight and small in size, such as in the case of a ventricle mirror electrode assembly. In this embodiment, the tip length of the electrode can be in a range of 2 mm to 4 mm. With the help of a small tip length, the tissue to be clamped can be clamped more accurately, so as to avoid undesirably clamping the surrounding tissue.

Since the inner tube 1018 has been compressed at the electrodes extending into the inner tube 1018 so as to press the distal end of the inner tube 1018 and the proximal ends of the electrodes 1015, 1016 together, narrowing of the distal end of the outer tube caused by the flat tapered structure 1040 may not hinder the relative movement of the inner tube 1018 and the outer tube 1017 in the longitudinal direction.

The following technical effect, for example, can be produced by the ventricle mirror electrode assembly: a wear-resistant protective element is provided, which simply and effectively solves the technical problem that electrode sleeves of an electrodes may be easily worn by the outer tube. Especially in the case of a ventricle mirror electrode assembly, walls of the electrode sleeves have a small thickness and are more likely to be worn out such that insulation ability thereof is damaged. In a common solution, one may usually try to use another material to form the electrode sleeves of the electrodes. However, due to the special requirements for electrode sleeves of a ventricle mirror electrode assembly, it is difficult to realize and is very costly, and it is difficult to find an ideal electrode sleeve material. However, the wear-resistant protective element of this embodiment can protect the electrode sleeves of the electrodes in a simple, reliable and low-cost manner, such that there is no need at all to consider the wear resistance of the electrode sleeve material, which broadens the material selection range. Besides, the arrangement of the tapered structure can achieve a better vision during surgery without providing any additional mechanisms and without varying other existing components, in the simplest and most reliable manner, which is very important to the clamping of a tissue by the electrode tips during surgery, can greatly improve the accuracy of clamping, increase the efficiency of the operation, and reduce the risk of misoperation.

The present disclosure may include any feature or combination of features implicitly or explicitly disclosed herein or a generic concept thereof, and is not limited to any defined scope as listed above. Any elements, features and/or structural arrangements described herein may be combined in any suitable manner.

The specific embodiments disclosed above are merely exemplary, and it will be apparent to those skilled in the art who benefit from the teachings herein that the present disclosure can be modified and implemented in different but equivalent manners. For example, steps of the above-mentioned method can be performed in a different order. It is therefore obvious that changes and modifications can be made to the specific embodiments as disclosed above, and all these variations are considered to fall within the scope and spirit of the present disclosure.

What is claimed is:

1. A surgical electrode assembly, the electrode assembly having a distal end farther away from an operator when in use and a proximal end closer to the operator when in use, wherein the surgical electrode assembly comprises:
    an electrode device disposed at a distal end of the electrode assembly, the electrode device comprising a first electrode and a second electrode, the first electrode and the second electrode being movable between a first position away from each other and a second position close to each other;
    a manipulating device disposed at a proximal end of the electrode assembly and configured to manipulate operation of the electrode device;
    an electrode driving device disposed between the manipulating device and the electrode device, configured to drive the first electrode and the second electrode of the electrode device to move between the first position and the second position with action of the manipulating device,
    wherein the electrode driving device comprises an outer tube and an inner tube, an outer diameter of the inner tube being smaller than an inner diameter of the outer tube, such that the inner tube is received inside the outer tube, such that the inner tube and the outer tube are movable relative to one another in a longitudinal direction of the inner tube and the outer tube, the inner tube having an inner tube proximal portion at a proximal end thereof, an inner tube distal portion of at a distal end thereof, and an inner tube bending portion therebetween, the inner tube bending portion having a curvature, such that the inner tube distal portion and the inner tube proximal portion are disposed at an angle to each other, and the outer tube having an outer tube proximal portion at a proximal end thereof and an outer tube distal portion at a distal end thereof, and an outer tube connecting portion therebetween, wherein the outer tube connecting portion is adapted to the inner tube bending portion, such that when manipulating the manipulating device to cause the inner tube and the outer tube to move relative to each other, the outer tube connecting portion allows the inner tube bending portion of the inner tube and the outer tube to move relative to each other in the longitudinal direction without interfering of the inner tube bending portion of the inner tube with the outer tube proximal portion and the outer tube distal portion of the outer tube, wherein the outer tube connecting portion is a tubular portion having an opening on the outer tube, and the inner tube bending portion of the inner tube is configured to be at least partially exposed from the opening; and wherein the opening is longitudinally and circumferentially sized to allow the inner tube bending portion of the inner tube to smoothly perform a relative movement in the longitudinal direction between the outer tube proximal portion and the outer tube distal portion of the outer tube without interfering with the outer tube proximal portion and the outer tube distal portion of the outer tube,
    wherein the manipulating device comprises a housing and an actuation mechanism at least partially disposed in the housing, and the actuation mechanism is adapted to actuate the electrode driving device, wherein the actuation mechanism comprises a crank device, a slider device operatively connected with the crank device, and a damping device, wherein the slider device has a rest position and a working position, wherein when there is no external force applied, damping effect of the damping device renders the slider device in the rest position, the slider device being operatively connected to the electrode driving device, and in the rest position of the slider device, the first electrode and the second electrode are in the first position away from each other, wherein an operator can apply a force to the crank device which in turn urges the slider device, such that the slider device is movable toward the working position, against the damping effect of the damping device, to thereby cause the first electrode and the second electrode of the electrode device to move from the first position to the second position, wherein, when the operator no longer applies a force to the crank device, the slider device moves toward the rest position with the action of the restoring force of the damping device, such that the first electrode and the second electrode of the electrode device move from the second position to the first position with action of their own elastic force, wherein the slider device urges and restores the crank device while moving toward the rest position, and wherein the slider device is operatively connected with the outer tube, such that the outer tube is movable with the movement of the slider device, and wherein the manipulating device further comprises a fixing block for fixing the inner tube in the housing, the fixing block being disposed at a distance proximal to the slider device.

2. The surgical electrode assembly according to claim 1, wherein when viewed into a cross section of the outer tube, the opening of the outer tube connecting portion occupies at least half of a circumference of the outer tube and exposes a convex side of the inner tube bending portion.

3. The surgical electrode assembly according to claim 1, wherein a portion of the inner tube distal portion and/or a portion of the inner tube proximal portion are exposed from the opening of the outer tube connecting portion.

4. The surgical electrode assembly according to claim 1, wherein there is always a distance from a distal edge and a proximal edge of the opening of the outer tube connecting portion to an apex of the inner tube bending portion when in use.

5. The surgical electrode assembly according to claim 1, wherein a distal edge and/or a proximal edge of the opening is curled inward or encapsulated, such that the distal edge and/or the proximal edge of the opening does not scratch a human body target tissue when contacting the human body target tissue.

6. The surgical electrode assembly according to claim 1, wherein the outer tube connecting portion is formed in one piece with the outer tube proximal portion and the outer tube distal end portion.

7. The surgical electrode assembly according to claim 1, wherein the distal opening of the outer tube is formed with an outward flange.

8. The surgical electrode assembly according to claim 7, wherein the inner tube bending portion and the outer tube connecting portion are each made of a flexible material in order to allow variation of a bending degree.

9. The surgical electrode assembly according to claim 7, wherein a bending degree of the inner tube bending portion and a bending degree of the outer tube connecting portion are variable in a range between 10° and 60°.

10. The surgical electrode assembly according to claim 7, wherein a bending degree of the inner tube bending portion and a bending degree of the outer tube connecting portion are variable in a range 30° and 40°.

11. The surgical electrode assembly according to claim 1, wherein the distal end of the outer tube has a flat tapered structure, the flat tapered structure including planes extending forward to gradually approach a centerline of the outer tube, and the planes being substantially perpendicular to the clamping surfaces for clamping the target tissue of the human body, of the distal portions of the first electrode and second electrode.

12. The surgical electrode assembly according to claim 1, wherein the inner tube bending portion has a bending degree and the outer tube connecting portion has a bending degree that are variable simultaneously.

13. The surgical electrode assembly according to claim 1, wherein, inside the inner tube, or between the inner tube and the outer tube, or outside the outer tube, a delivery passage is provided for delivering a flushing liquid is provided.

14. The surgical electrode assembly according to claim 1, wherein the first electrode and the second electrode are fixed to the inner tube by an adhesive.

15. The surgical electrode assembly according to claim 1, wherein the distal portions of the first electrode and the second electrode are bent upward, downward or formed straight.

* * * * *